United States Patent [19]
Siczek et al.

[11] Patent Number: 5,008,919
[45] Date of Patent: Apr. 16, 1991

[54] X-RAY FILM CHANGER POSITIONING DEVICE

[76] Inventors: Aldona A. Siczek; Bernard W. Siczek, both of 1252 Chinook Way, Boulder, Colo. 80303

[21] Appl. No.: 529,551

[22] Filed: May 29, 1990

Related U.S. Application Data

[63] Continuation of Ser. No. 398,834, Aug. 25, 1989.

[51] Int. Cl.⁵ ............................................. G03B 42/02
[52] U.S. Cl. .................................... 378/173; 378/167; 378/181
[58] Field of Search ................ 378/173, 172, 167, 181

[56] References Cited

U.S. PATENT DOCUMENTS

| | | | |
|---|---|---|---|
| 4,198,566 | 4/1980 | Nieminen | 378/181 |
| 4,260,896 | 4/1981 | Schmidt | 378/173 |
| 4,879,736 | 11/1989 | Bergman et al. | 378/181 |

Primary Examiner—Edward P. Westin
Assistant Examiner—Kim-Kwok Chu

[57] ABSTRACT

An X-ray examination apparatus includes a device for positioning an X-ray film changer with respect to an image intensifier away from a position in front of the image intensifier for producing X-ray images to a position on a side of the image intensifier when not in use. The device combines a rotational and shifting movement so that the film changer can be positioned on the side of the image intensifier very close to the same without impeding access to a patient.

1 Claim, 1 Drawing Sheet

X-RAY FILM CHANGER POSITIONING DEVICE

This is a continuation of Ser. No. 07/398,834, filed 08/25/89.

FIELD OF INVENTION

This invention relates to a mechanism for positioning a film changer with respect to an image intensifier in an X-ray apparatus using same.

BACKGROUND OF INVENTION

In an X-ray imaging apparatus, which includes an image intensifier with an X-ray film changer, it is desirable to effectively reposition the film changer from a position in front of the image intensifier screen to produce X-ray images to a standby position away from the screen when not in use.

SUMMARY OF INVENTION

This invention provides for a mechanism and a device for positioning an X-ray film changer used in conjunction with an image intensifier from a position in front of the image intensifier screen to a position away from the screen when not in use.

BRIEF DESCRIPTION OF THE DRAWING

The accompanying drawing illustrates a presently preferred embodiment of the invention according to the mode so far devised for practical application of the principle thereof, and in which:

DESCRIPTION OF THE DRAWING

Figure 1:
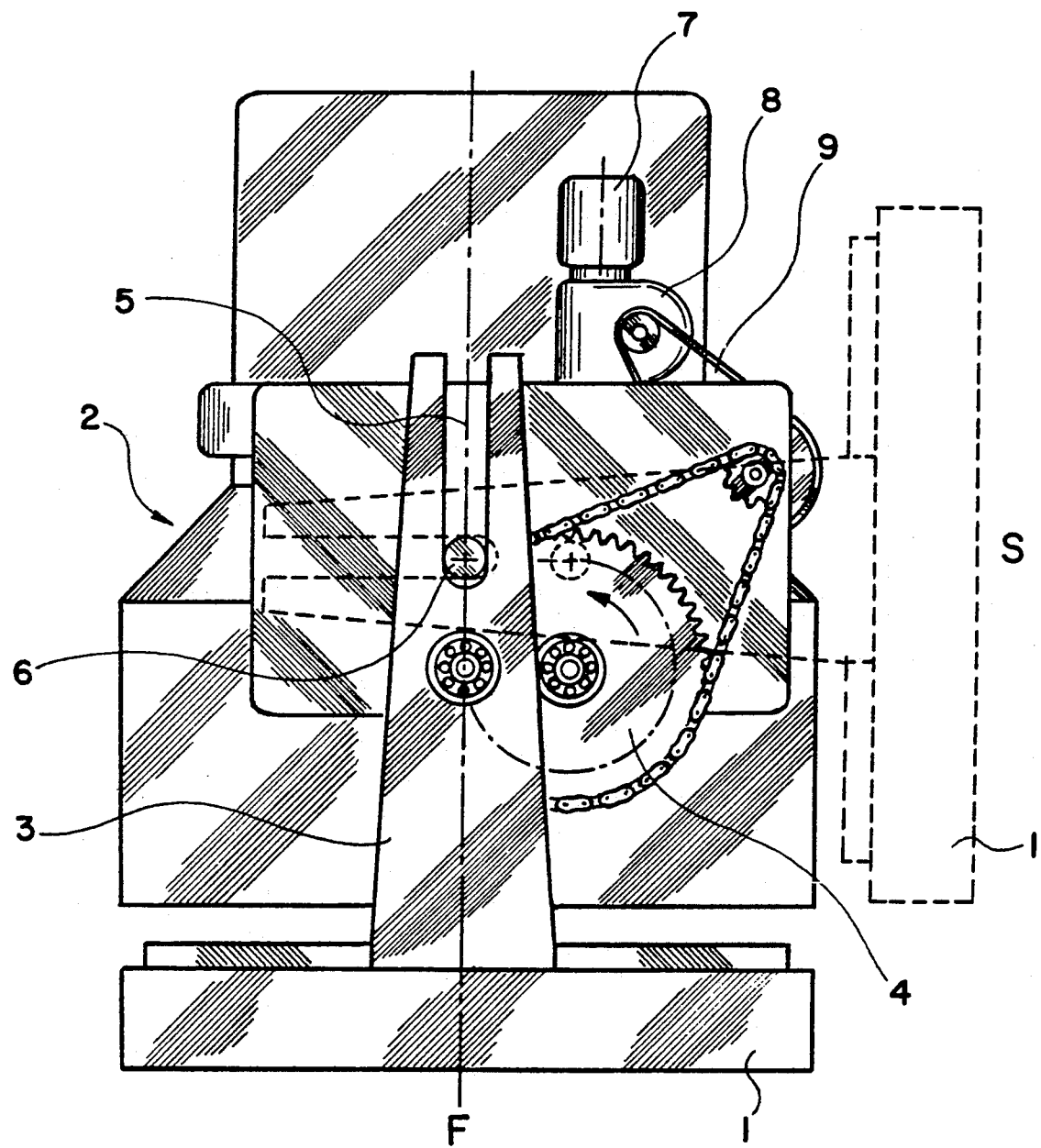
FIG. 1 illustrates an X-ray film changer positioning device.

FIG. 1 shows a film changer positioning device to displace the film changer 1 from a position F in front of a screen of an image intensifier 2 to a position S away from this screen on a side of the image intensifier (shown in a broken line). This positioning device comprises a pair of support members 3 supporting the film changer and extending therefrom, each of which support member is secured to the image intensifier 2 by a rotary member 4 in a pivoting relationship about an axis parallel to and offset from an axis of rotation of this rotary member and includes a linear guide 5 disposed at one extremity thereof opposite to the film changer, which linear guide is engaged respectively by a stationary post 6, whereby rotation of the rotary member, caused by energizing a motor 7 with a reducer 8 and a transmission 9, changes position of the film changer from one position offset from the axis of the rotary member to another position offset from the axis of the rotary member, that is from F to S and from S to F.

We claim:

1. In an X-ray imaging apparatus which apparatus includes an image intensifier and a film changer, a film changer positioning device comprising at least one supporting member supporting said film changer and extending therefrom, said supporting member secured to said image intensifier by a rotary member in a pivoting relationship about an axis parallel to, and offset from, an axis of rotation of said rotary member and including a linear guide disposed at one extremity thereof opposite to said film changer, which linear guide is engaged by a stationary post, whereby rotation of said rotary member changes position of said film changer from one position offset from the axis of rotation of the rotary member to another position offset from said axis of rotation.

* * * * *